United States Patent
Keefe et al.

(10) Patent No.: US 9,830,521 B2
(45) Date of Patent: Nov. 28, 2017

(54) MEDICINAL SUBSTANCE IDENTIFICATION BASED ON CONTAINER RECOGNITION

(71) Applicant: Codonics, Inc., Middleburg Heights, OH (US)

(72) Inventors: Gary Keefe, Brecksville, OH (US); Lawrence Srnka, Northfield Center, OH (US); Peter Botten, Lakewood, OH (US)

(73) Assignee: CODONICS, INC., Middleburg Heights, OH (US)

( * ) Notice: Subject to any disclaimer, the term of this patent is extended or adjusted under 35 U.S.C. 154(b) by 0 days.

(21) Appl. No.: 14/892,102

(22) PCT Filed: May 19, 2014

(86) PCT No.: PCT/US2014/038594
§ 371 (c)(1),
(2) Date: Nov. 18, 2015

(87) PCT Pub. No.: WO2014/189834
PCT Pub. Date: Nov. 27, 2014

(65) Prior Publication Data
US 2016/0092744 A1 Mar. 31, 2016

Related U.S. Application Data

(60) Provisional application No. 61/825,011, filed on May 18, 2013.

(51) Int. Cl.
*G06K 9/18* (2006.01)
*G06F 19/00* (2011.01)
(Continued)

(52) U.S. Cl.
CPC ....... *G06K 9/183* (2013.01); *G06F 17/30268* (2013.01); *G06F 19/321* (2013.01);
(Continued)

(58) Field of Classification Search
CPC .......... G06K 9/183; G06K 9/20; G06Q 50/22; G06F 19/3456; G06F 19/3462;
(Continued)

(56) References Cited

U.S. PATENT DOCUMENTS 7,559,483 B2   7/2009 Hickle
8,738,177 B2 * 5/2014 van Ooyen ......... G06F 19/3462
                                                              700/235
(Continued)

FOREIGN PATENT DOCUMENTS

WO     2011/046725 A2    4/2011

OTHER PUBLICATIONS

International Search Report issued in Application No. PCT/US2014/038594 dated Sep. 11, 2014.
(Continued)

*Primary Examiner* — Ali Bayat
(74) *Attorney, Agent, or Firm* — Cooper Legal Group, LLC

(57) ABSTRACT

Provided is a system for identifying a drug container that includes an image capture device configured to capture an optical image of a portion of a label provided to the drug container, and a non-transitory computer storage medium storing a plurality of features for each of a plurality of different drugs included in a database. The features associated with each of the plurality of different drugs are suggestive of an identity of a drug identity but do not, alone, positively identify the drug identity. A processing component is configured to receive data representing the optical image transmitted by the image capture device and to identify a candidate for the drug identity based on the plurality of features associated with the candidate.

20 Claims, 11 Drawing Sheets

(51) Int. Cl.
*G06K 9/00* (2006.01)
*G06F 17/30* (2006.01)
*G06K 9/20* (2006.01)

(52) U.S. Cl.
CPC ........... *G06F 19/3462* (2013.01); *G06K 9/00* (2013.01); *G06K 9/20* (2013.01)

(58) Field of Classification Search
CPC ...... G06F 19/326; G06F 19/30; G06F 19/321; G06F 17/30247; G06F 17/30268; G06F 17/30312
See application file for complete search history.

(56) References Cited

U.S. PATENT DOCUMENTS

| | | | |
|---|---|---|---|
| 2007/0213684 A1* | 9/2007 | Hickle | A61J 1/14 604/500 |
| 2008/0314978 A1 | 12/2008 | Fedorko | |
| 2012/0004770 A1* | 1/2012 | Ooyen | G06F 19/3462 700/235 |
| 2012/0201434 A1 | 8/2012 | Natali | |
| 2014/0156294 A1* | 6/2014 | Tribble | G06F 19/326 705/2 |
| 2015/0019008 A1* | 1/2015 | van Ooyen | G06F 19/3462 700/235 |
| 2016/0055317 A1* | 2/2016 | Levine | G06F 19/326 705/2 |

OTHER PUBLICATIONS

Written Opinion issued in Application No. PCT/US2014/038594 dated Sep. 11, 2014.

* cited by examiner

ABSTRACT# MEDICINAL SUBSTANCE IDENTIFICATION BASED ON CONTAINER RECOGNITION

BACKGROUND OF THE INVENTION

1. Field of the Invention

This application relates generally to a method and apparatus for identifying a medicinal substance and, more specifically, to a method and apparatus for capturing and utilizing one or more optically-observable features of a container storing the medicinal substance to at least narrow a list of potential candidates from which the identification of the medicinal substance can be selected.

2. Description of Related Art

Conventional drug vials, for example, typically include a label identifying the drug stored therein. The label can also include other information such as the concentration of the drug. Retrieving the proper vial to extract a desired amount of the medicinal substance from a pharmacy or other drug depot is commonly left to the ability of the clinician, who will make the selection based on the content appearing on the label.

However, one vial will often be selected from a large collection of vials storing different drugs, possibly bearing labels having an appearance similar to each other in many respects. Human error remains a possibility that could result in the selection of the wrong vial. And although barcoding is becoming a widely-adopted practice to expressly define the drug contained in the vial, labels can be damaged in transit and rendered difficult to accurately read.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
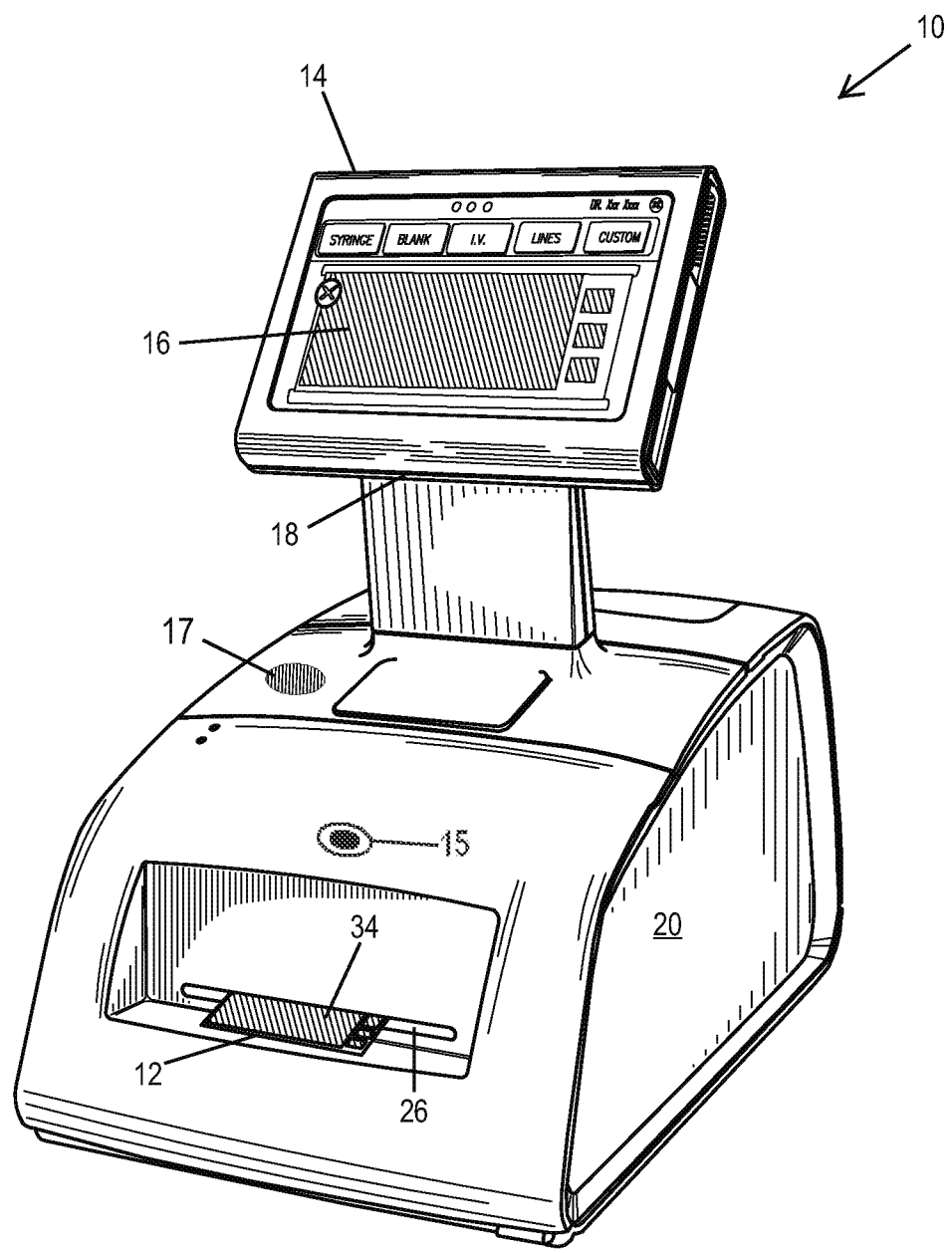
FIG. 1 shows an illustrative embodiment of a label recognition apparatus that recognizes one or more features associated with a label applied to drug vial, and/or the vial itself, in an effort to identify a drug stored in the drug vial.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

An illustrative embodiment of a label recognition terminal 10 is shown in FIG. 1. The label recognition terminal 10 includes a touch-screen display 14 coupled to a cabinet 20 to display a virtual label 16 comprising label content 34 identifying the drug to be administered to a patient, and optionally other information describing the dose of the drug to be administered to a patient as described below. The label content 34 displayed on the virtual label 16 and optionally printed onto a label 12 to be applied to a delivery container for the drug is generated based, at least in part, on an optically-captured image of a label provided to a drug vial 21 (FIGS. 3-6) and/or manually-entered drug information.

The label recognition terminal 10 can be operable to scan a computer-readable code and print a label to be applied to a medical container such as a syringe as described in U.S. patent application Ser. No. 12/901,110, which is incorporated by reference herein in its entirety. The display 14 can display soft keys that, when touched by a technician or any other user, inputs data and commands into the label recognition terminal 10. The virtual label 16 is a computer-generated rendering of the label 12, as opposed to the actual label 12 bearing the printed label content, that offers the user an opportunity to visually confirm that the label content 34 to be printed is correct before the label 12 is printed by a printer 26. A computer-input peripheral such as a non-contact scanner 18 can be provided at a convenient location, integrally formed in a bottom portion of the display 14 to read a machine-readable code supported beneath the scanner 18, for example. Integrally forming the scanner 18 as part of the display 14 provides for space savings over an arrangement where the scanner 18 is formed as a separate peripheral, which can be repositioned relative to the display 14. However, other embodiments can allow for a separate and distinct scanner 18 and/or display 14. Additionally, the scanner 18 can be separable from the cabinet 20.

The computer-input peripheral can be a barcode reader or radio-frequency identification ("RFID") tag reader, or any other device that reads a machine-readable code such as a barcode or RFID code, respectively, or any other machine-readable code without requiring contact between the computer terminal and the code, and optionally the user during entry of the code. According to alternate embodiments, the display 14 can be utilized by a user as a computer-input peripheral. For such embodiments, the soft keys displayed by the display 14 can be selected to input information such as a medicinal substance being prepared to be administered to a patient or other information to be utilized in generating the label as described herein. According to yet alternate embodiments, a speaker 17 can optionally be provided to the display 14 or any other portion of the label recognition terminal 10 to broadcast audible sounds.

Figure 2:
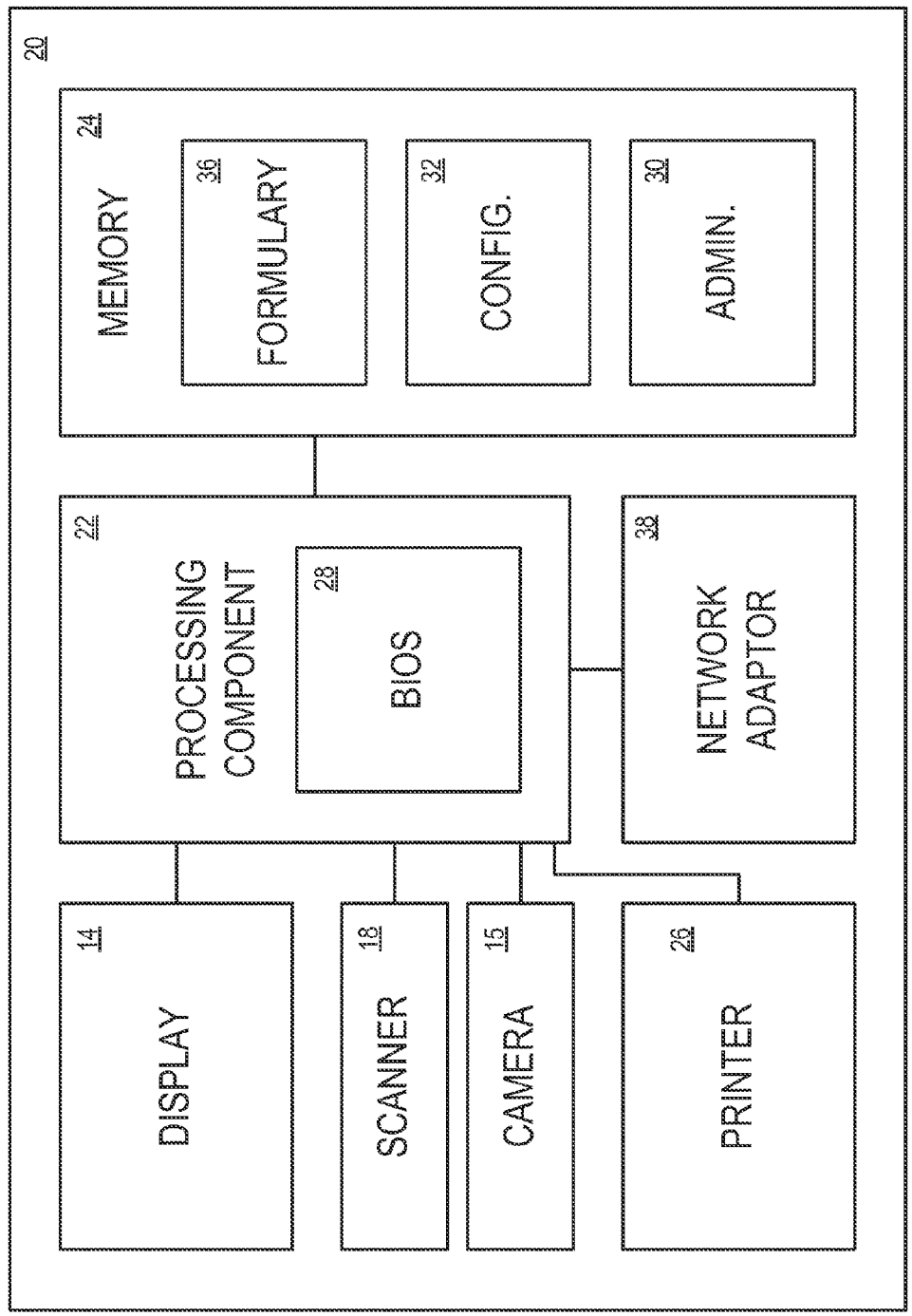
FIG. 2 shows a block diagram schematically depicting components of a label recognition apparatus for generating labels to be applied to medicinal substances in a medical facility.
Figure 3:
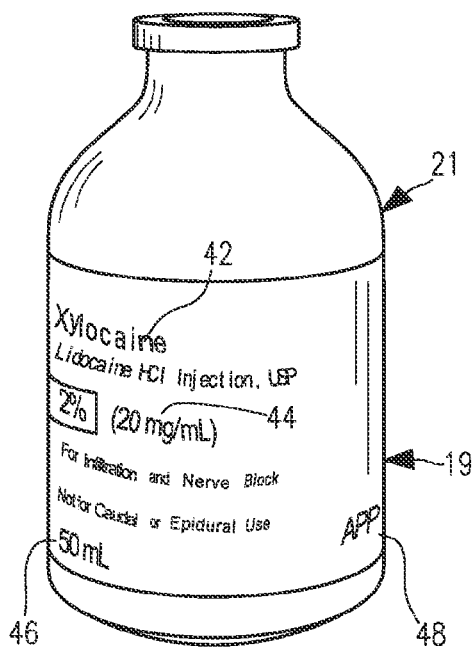
FIGS. 3-6 show illustrative embodiments of different drug vials, each bearing a label for a different drug.

In addition to, or instead of the scanner 18, the input/output system of the label recognition terminal 10 can include a camera 15 for capturing an optical image (e.g., photograph) of a portion of a commercial label 19 provided to a drug vial 21 or other container by a distributor or source of the drug and received by the medical facility, and optionally a portion of the drug vial 21 or other container itself. The camera 15 can include any suitable imaging sensor (e.g., digital charge-coupled device "CCD", complementary metal-oxide-semiconductor "CMOS", and the like) for recording the optical image and a lens assembly through which light en route to the imaging sensor enters the camera 15. The scanner 18 interrogates barcodes or otherwise recognizes computer-interpreted patterns or reads electronic data formatted specifically in a computer-readable form that allows the label recognition terminal 10 to read the underlying data and expressly and definitively identify the drug. In contrast, the camera 15 captures and stores an electronic image or graphic that visually resembles the portion(s) of the label 19 and/or drug vial 21. The captured image or graphic is stored in a non-transitory, computer-readable memory 24 (FIG. 2), from where the image or graphic can be retrieved and subjected to processing operations under the control of a processing component 22 (FIG. 2) of the label recognition terminal 10 executing computer-executable instructions.

The cabinet 20 of the label recognition terminal 10 also houses or supports components that are operable to produce an after-market, or on-demand label 12 in compliance with a medical labeling standard at a time when the drug is to be withdrawn from the vial 21 to be administered to a patient. But if what is being labeled is anything other than the medicinal substance, then the label 12 produced is to be compliant with a standard developed by a trade or professional organization, governing body, government agency, a healthcare provider or facility such as a hospital, or any other standards body setting forth policies for labeling such material. Such internal components housed within the cabinet 20 are schematically illustrated by the block diagram of FIG. 2. The components can be formed from an arrangement of computer hardware such as ASICs, computer processors, programmable logic controllers and other circuitry; or a combination of computer hardware and computer-executable instructions. For example, the processing component 22 is provided to execute computer-executable instructions stored in the non-transitory, computer-readable memory 24 such as a hard disk drive, read-only memory ("ROM"), random access memory ("RAM"), optical disc, or any other suitable memory device, or any combination thereof. The computer-executed instructions, when executed by the computer processor 22, result in the performance of the method of generating a label 12 for a medicinal substance. A BIOS 28 is provided to load the operating system and other such administrative instructions 30 stored in the memory 24 and manage hardware interface permissions of the label recognition terminal 10. The operating system can be configured to only load authorized updates to prevent unauthorized changes to a formulary 36 of drugs stored in the memory 24, configuration data 32 and administration instructions 30. Configuration data 32 controls various features of the label recognition terminal 10 that are active and available for use at any given time. The configuration data 32 can optionally be stored, updated and deleted from the memory 24 by the introduction of a so-called smart drive comprising a USB compatible flash memory to the label recognition terminal 10. When the smart drive is introduced to the label recognition terminal 10, it establishes the configuration data 32 of the label recognition terminal 10. The configuration data 32 can optionally be used to deactivate functional features that the label recognition terminal 10 would otherwise be able to perform based on the model of the label recognition terminal 10 purchased. Accordingly, a common hardware platform of the label recognition terminal 10 can be configured in a plurality of different functional configurations based on the configuration data 32.

In addition to the administrative instructions 30, the memory 24 also stores an updatable formulary 36 containing a database of medicinal substances that can be identified by the label recognition terminal 10 and select information for each medicinal-substance entry in the database. The formulary 36 can optionally be stored, updated and deleted from the memory 24 by the introduction of a so-called smart drive comprising a USB compatible flash memory to the label recognition terminal 10, and define the drugs that can possibly be identified as described below using the label recognition terminal 10. In other words, the label recognition terminal 10 can optionally be limited to printing standard-compliant labels 12 for those drugs included in the formulary 36. When the smart drive is introduced to the label recognition terminal 10, it establishes the formulary 36 of the label recognition terminal 10. Illustrative examples of the select information that can be provided for the medicinal-substance entries includes, but is not limited to, an ID number such as a NDC code, UPC code, EAN code, or any other identifying data that can be used to relate a barcode or other computer-readable code to the medicinal-substance entries; a sound file that, when played, audibly announces the name of the medicinal substance identified in response to scanning a machine readable code; warning data; or any combination thereof.

A network adaptor 38 is operatively connected to communicate with the processing component 22 for translating signals received by the label recognition terminal 10 over a communications network (e.g., LAN, WAN such as the Internet, etc. . . . ) at a medical facility. The network adaptor 38 can be compatible with any type of network communication. For example, the network adaptor 38 can include a hardwired, 10Base-T, 100Base-T, or 1000Base-T Ethernet interface with an RJ-45 socket, a coaxial cable interface, a fiber-optic interface, any format of wireless communication interface such as an antenna compatible with any of the 802.11 standards established by the IEEE, or any combination thereof. Embodiments including wireless network adaptors 38 can employ any desired securing protocol such as WEP, WPA and WPA2, for example, and other suitable security protocol. For embodiments including a network adaptor 38 compatible to communicate over a plurality of different network communication channels, both a hard-wired communication portion of the network adaptor 38 and a wireless communication portion of the network adaptor 38 can optionally be concurrently active. Thus, the label recognition terminal 10 can optionally communicate via both the hard-wired and wireless portions of the network adaptor 38 concurrently.

The formulary 36 stored in the memory 24 is a database that includes a compilation of drugs, at least some of which are used in the medical facility where the label recognition terminal 10 is located. In addition to the identity of each drug, the record for each drug in the formulary 36 can independently be configured to include at least one of a: concentration; weight; dilution information; manufacturer's identity; code; label 19 size and/or shape information indicating the size and/or shape of a label 19 adorning a vial 21 storing the respective drug; vial 21 size and/or shape information about the size and/or shape of the vial 21 storing the respective drug; label content information identifying at least one observable property of label content included on the label 19 adorning a vial 21 storing the respective drug; an image of the label 19, the vial 21, or both the label 19 and the vial 21; and any other distinctive feature useful for distinguishing between vials or other containers of different drugs.

Labels provided to drug vials identifying the drugs stored therein may include distinctive features that, when observed by a human clinician, assist in distinguishing the vials containing different drugs from each other. In contrast to the barcodes read by the scanner 18, these distinctive features are not specifically adapted to facilitate interpretation by a computer to explicitly and definitively identify the drug. Instead, they are in a human-observable/interpretable format, intended by the party generating the label content for observation, and optionally interpretation, by a human clinician viewing the label without the aid of a computer or other device.

For example, as shown in FIGS. 3-6, the drug name 42 (which can be a scientific name of the chemical or a commercial trade-name given to the commercially-available product) is printed on the label 19 as a string of letters that can be read by the clinician. Additionally, the concentration 44, volume 46 of the drug in the vial and, in some instances (FIGS. 3-5), the identity of the manufacturer 48 or the party on whose behalf the drug was manufactured appear in human-readable characters. Such characters can be extracted from the image captured by the camera utilizing an optical-character-recognition ("OCR") technique, optionally after being subjected to a pre-OCR processing step such as rotating the captured image to orient the characters in a desired orientation for the OCR technique and for standardized comparison to entries in the formulary 36.

Figure 4:
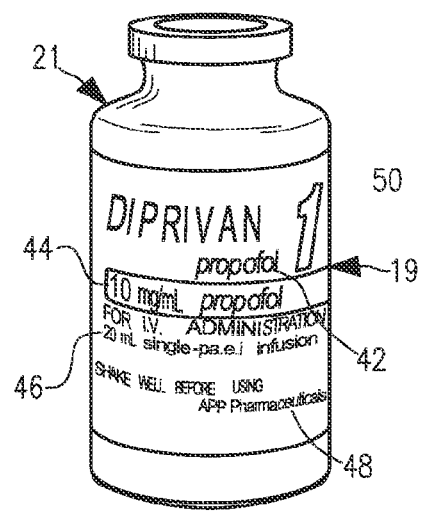
Figure 5:
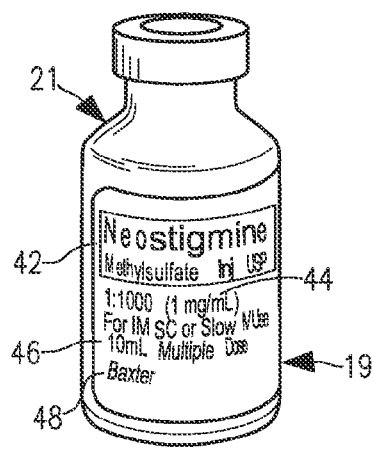
Figure 6:
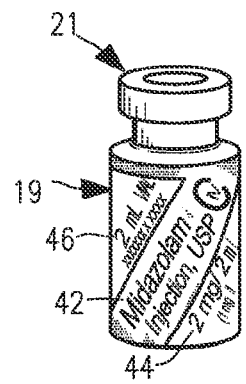

In addition to the alpha and/or numeric characters, decorative label content can also be considered as a distinctive feature. For example, the font and/or size of text used for the characters appearing on the label, the negative representation of characters indicating the concentration 44 as shown in FIG. 4 and the drug name 42 in FIG. 5, a graphic 50 (FIG. 4) appearing as part of the label content, the arrangement of the label content (the drug name 42 and concentration 44 arranged diagonally across the label 19 in FIG. 6 for example), any other feature that can be optically observed and extracted from an image of the label 19 captured by the camera 15, or any combination thereof can be considered as a distinctive feature in narrowing the list of possible matching drugs in the formulary to a manageable number.

In addition to the distinctive features appearing as printed label content, the size, shape, or both the size and shape of the label 19 provided to a drug vial 21 can be included in the distinctive features considered as described below in an effort to identify the drug in the vial 21. For instance, in FIGS. 3-6 the label 19 provided to each respective vial 21 covers its respective vial 21 to a different extent. The label 19 in FIG. 6 conceals all but the neck of the vial 21, while the label 19 in FIG. 3 conceals a mid region of the vial 21, but leaves a substantial portion of the vial 21 between the top of the label 19 and the neck unobstructed. According to alternate embodiments, the camera 15 can be utilized in conjunction with a range finder (e.g., capacitive sensor, a graduated measuring device such as a ruler positioned a fixed distance in front of the camera where the label 19 and vial 21 are to be positioned while the image is captured) to establish a reference for objectively evaluating the size of the label 19 and/or vial 21. This objectively-evaluated size can also be considered as a distinctive feature.

The vial size and/or shape information can also be extracted from the image of the vial 21 captured by the camera 15 to be considered as a distinctive feature in identifying the drug. This information can include at least one of a height, width, shape, aspect ratio, and color of the portion of the vial 21 appearing in the image captured by the camera 15.

Each such distinctive feature was supplied to the medical facility as part of the labels 19 and/or vials 21 by the respective supplier of the drug to be observed by human clinicians reading the label with the naked eye. The distinctive features also were not printed, manufactured or otherwise specifically adapted to encode information about the drug in a computer-readable format. In other words, the distinctive features collectively convey an overall appearance of the label and/or drug vial to a human observer, and do not serve a separate, dedicated purpose of conveying information to a computer terminal in a computer-readable/interpretable format. However, the distinctive features can be captured in, and recognized from a digital image captured by the camera 15.

The formulary 36 stored in the memory 24 can be an evolving work that is updated over time. Updates to the formulary 36 can occur as the result of manual entry of information by a party at the medical facility with the requisite level of authority. For instance, a digital photograph of a vial 21, including at least a portion of the label 19 provided to that vial 21, can be taken upon receiving the vial 21 storing the drug at the medical facility. This digital photograph can be stored in the formulary 36 associated with the respective drug entry for the drug stored in the vial 21.

Additionally, each time a clinician confirms that an image captured using the camera 15 identifies a drug included in the formulary 36, the formulary 36 can be updated to reflect this confirmation so that future identifications based on the captured image, as described below, can be made with improved certainty. According to such embodiments, the image confirmed by the clinician to identify the particular drug can be stored in the formulary entry corresponding to that particular drug in response to receiving the clinician's confirmation. This confirmed image can optionally update an existing image in the formulary 36, such as when the drug is purchased from a new source in a differently-labeled vial 21, or when the label 19 from the existing supplier includes an appearance that has changed relative to a previous version of the label 19.

Figure 7:
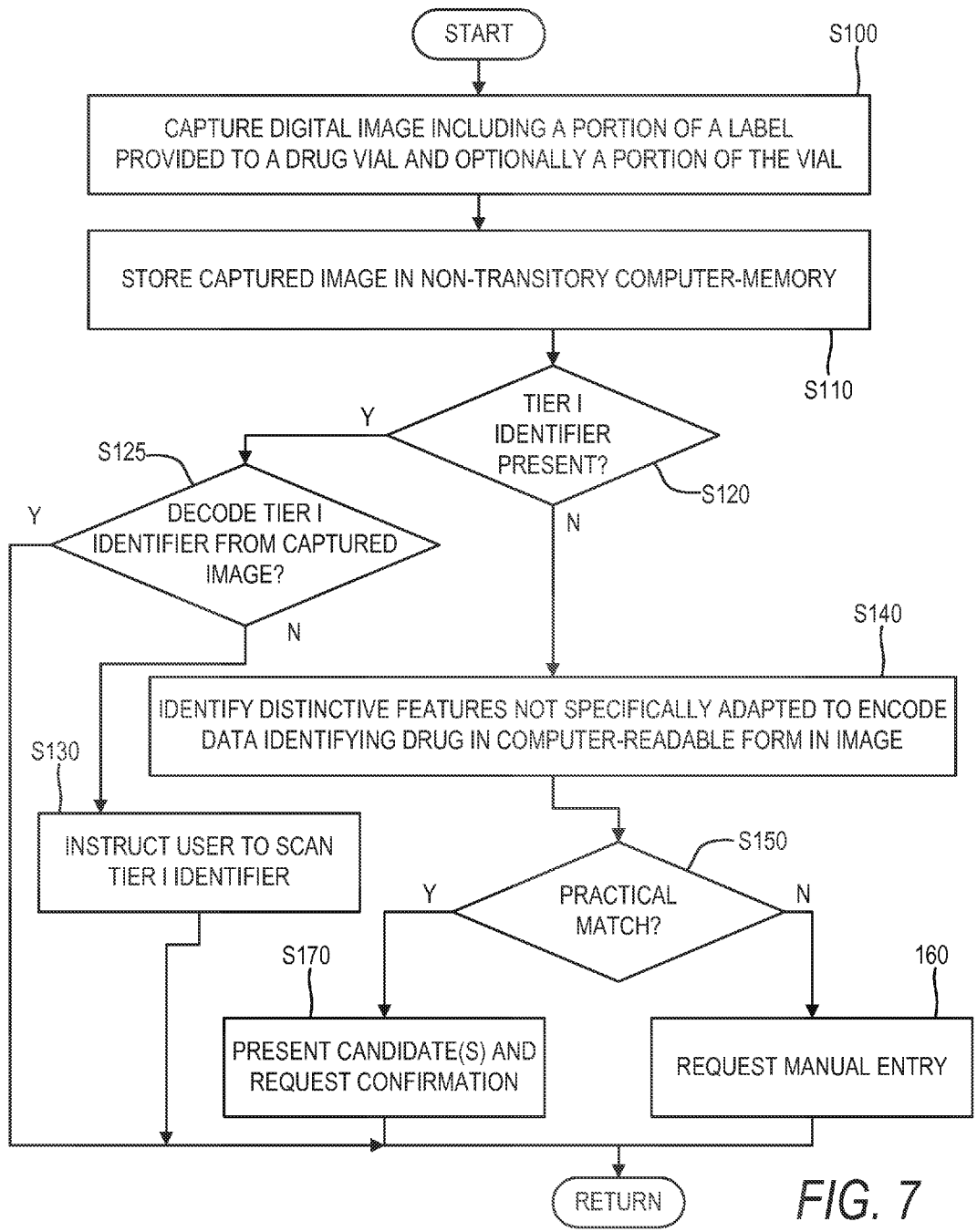
FIG. 7 is a flow diagram schematically illustrating a method of identifying a drug.

An illustrative description of the label recognition terminal 10 in use to identify, or at least narrow the drugs in the formulary 36 to a practical number of potentially-matching candidates is described with reference to FIG. 7. At step S100 a digital image of a portion of a label 19, and optionally the vial 21 with the label 19, and the image is stored in the memory 24 at step S110. The image is evaluated and examined to determine if what is referred to herein as a "Tier I" identifier is present in the captured image. A Tier I identifier is a computer-readable code such as a barcode, for example, that uniquely and definitively encodes information such as the identification of the drug, resulting in a Tier I match. If a Tier I identifier is determined to be present, at step S125 an attempt can be made to decode the Tier I identifier in the case of a barcode or other optically-detectable encoded symbol. If it is determined at step S125 that the attempt was successful, the corresponding drug can be identified from the formulary via a lookup operation, query-retrieve, etc. . . . or otherwise relating the decoded information from the Tier I identifier to the corresponding drug. If, on the other hand, the Tier I identifier was unable to be decoded from the captured image, the label recognition terminal 10 can alert the clinician to the presence of the Tier I identifier in the captured image and instruct the clinician to interrogate or otherwise evaluate the Tier I identifier utilizing a compatible decoder. Since a Tier I identifier, if present, can be scanned using the scanner 18 to uniquely identify the drug with near certainty for example, the display 14, speaker 17 or other output device provided to the label recognition terminal 10 can instruct the clinician to scan the Tier I identifier with the scanner 18 to obtain the identity of the drug at step S130.

If, at step S120, a Tier I identifier that would result in a Tier I match is not found in the captured image, the processing unit 22 can execute a process utilizing computer-executable instructions stored in the memory 24 to evaluate the captured image at step S140 and identify one or more so-called "Tier II" identifiers, if present. A Tier II identifier includes one or more of the distinctive features described above that, when read by the human clinician with the naked eye, would uniquely identify the corresponding drug to the clinician. For the present embodiment, the Tier II identifiers can include the drug name and the drug concentration appearing on the label in human-readable characters (e.g., alpha and/or numeric characters). Such features were not included as part of the label 19 and/or vial 21 from the source of the drug with the intent of being evaluated by a computer and used to identify the drug. Instead, the Tier II identifiers are generally provided as part of the label 19 and/or vial 21 for observation by a human user with the naked eye. To be evaluated by the label recognition terminal 10, those characters must first be subjected to the OCR processing step or otherwise converted from a strictly human-readable format into a format that can be recognized and parsed by the label recognition terminal 10. Once converted, these Tier II identifiers can optionally be processed by the processing unit 22 and optionally "learned" (i.e., confirmed as being associated with a drug in the formulary) over time by the label recognition terminal 10 and stored as part of the formulary 36 in association with its respective drug. The converted Tier II identifiers can be collectively considered together by the label recognition terminal 10 to identify the drug and its concentration with reasonable accuracy, although less than certain. Identifying the drug and optionally its concentration in this manner based on the Tier II identifier(s) can be presented to the clinician via the display 14 and/or speaker 17 of the label recognition terminal 10 for confirmation, which can optionally be required to be input by the clinician prior to printing the label 12 for the identified drug and/or concentration. A single Tier II identifier, by itself and when used independently of a Tier I identifier, does not necessarily result in a definitive identification of the corresponding drug and its concentration (or other property of the drug) due to limited accuracy of the processing operations performed by the processing unit 22 and because a Tier II identifier may not be unique to a given drug. For instance, more than one vial of a specific drug may be present in the formulary, but at different concentrations. Thus, identifying the drug based on its name may result in each of the available concentrations being presented to the clinician via the display 14, for example, thereby allowing the clinician to manually select the proper concentration. Although a single Tier I identifier can uniquely identify the drug and its concentration, both Tier II identifiers (drug name and drug concentration) must be utilized to uniquely identify the drug.

The accuracy of an identification based on a Tier II identifier can depend on the accuracy of the OCR operation or other processing step performed to convert the otherwise human-readable label content into a computer-interpretable form. Accordingly, one or a plurality of candidates selected from the formulary 36 as potentially being a match for the drug in the vial 21 associated with those Tier II identifiers will each have a likelihood of being a match that is less than certain, which is the likelihood of a match based on a Tier I identifier. For example, to be considered a Tier II match based on one or both Tier II identifiers, the likelihood that a candidate has positively been identified as the drug in the vial 21 can fall within a range from about 50% to about 99%, for example.

Tier III identifiers can include any one or more of the other distinctive features appearing on the label 19 and/or vial 21 that even if observed by the clinician, would not by themselves uniquely identify the drug but may provide suggestive clues as to the identity of the drug. For example, a particular font, color, label size, character arrangement, pattern vial size and/or shape, etc. . . . may be used for storing and/or labeling different drugs. Even when considered together, such Tier III features will not uniquely identify the drug and its concentration. The label recognition terminal 10 can recognize such Tier III identifiers, and can consider those in combination with Tier II identifiers when narrowing the list of candidates, but a unique and definitive identification of the drug cannot be made solely on the basis of a combination of Tier III identifiers.

Once a Tier II identifier has been detected in the captured image, the label recognition terminal 10 determines, at step S150, whether a practical number of potential matches have been identified. For instance, an error occurs during the OCR process or if certain characters are not conducive to being converted, for example, and 1,000 potential matches are identified based on the Tier II identifiers, it would be unreasonable to expect the clinician to review the entire list of potential matches and confirm the identity of the drug through manual inspection (i.e., with the naked eye) of the label 19. Such a list can be filtered based on any Tier III identifiers found in the captured image, and only those potential matches with the greatest likelihood of being the actual drug can be presented to the clinician. But even after filtering, there may be 500 potential matches, each with a 75% likelihood of being the actual drug. Again, such a result would not be practical. Embodiments of the label recognition terminal 10 can optionally consider a practical match to be a list of 10 or fewer potential matches, or optionally 5 or fewer potential matches, or optionally a number of matches no greater than the number that can be concurrently displayed by the display 14.

If, at step 150 it is determined that a match is not practical, or if a distinctive feature is not found in the captured image at step S140, the match is determined to lack sufficient reliability to be of any use to the clinician. As a result, the clinician is requested to manually enter the identification of the drug at step 160, which can optionally be performed as discussed in detail below.

If, however, the match is determined to be practical at step S150, the label recognition terminal 10 presents, at step S170, the one or more candidates with the greatest likelihood of matching the drug to the clinician via the display 14. The candidates can be different drugs, or the same drug at different concentrations. The clinician can touch the matching candidate if the display 14 is a touch-sensitive display or otherwise enter confirmation of the matching candidate via another input peripheral. In response to receiving the confirmation, the formulary 36 can be updated to improve the relationship between the Tier II identifiers (and optionally any Tier III identifiers detected and utilized by the label recognition terminal 10 to identify the drug and its concentration) detected in the captured image and the match manually confirmed by the clinician. This relationship can also be improved based on a frequency and/or a number of times that the match in question is manually confirmed as correctly identifying the actual drug. Thus, if a clinician who is logged into the label recognition terminal 10 routinely uses a particular drug as part of his/her medical practice, or uses a particular drug many more times than another similar drug that may share some of the same Tier II identifiers, the likelihood that the frequently-used drug or the drug used several times in the past is the actual match will be greater than the likelihood assigned to the other drug not used as frequently or as many times. Since clinicians can be required to log into their user accounts when using the label recognition terminal 10, this preference can be customized on a clinician-by-clinician basis to reflect each of their individual practices.

Figure 8:
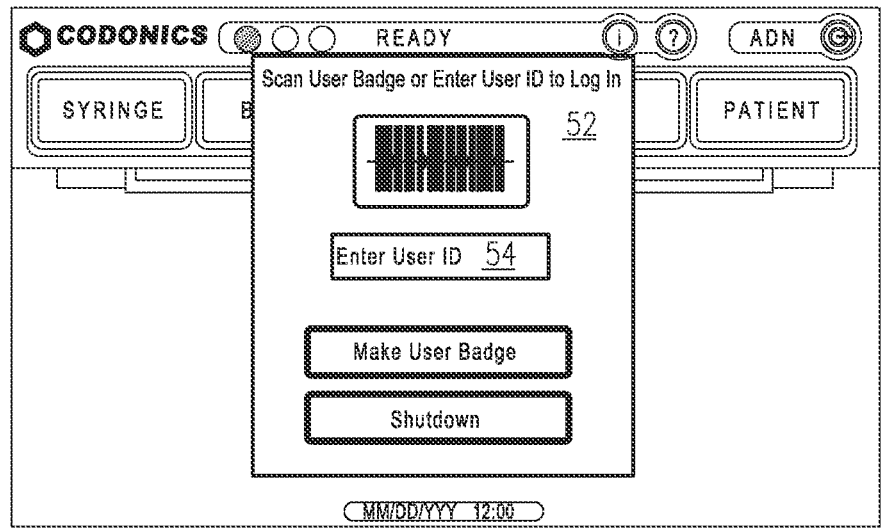
FIG. 8 shows an illustrative embodiment of a login screen of a label recognition device.

The label recognition terminal 10 can also be used to manually narrow the full listing of drugs in the formulary 36 to identify the actual drug in a stepwise process. As shown in FIG. 8, a login screen 52 displayed by the display 14 includes a manual entry field 54 in which the clinician logging in can enter a unique user identification. Alternately, the clinician can scan a barcode on the clinician's identification badge using the scanner 18 to log in.

Figure 9:
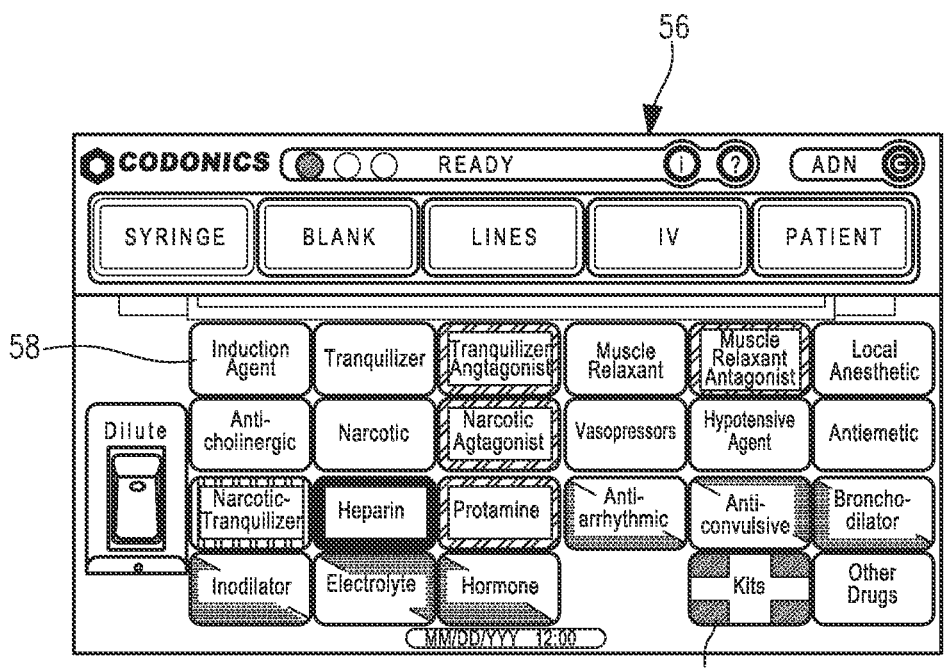
FIG. 9 shows an illustrative embodiment of a home screen presenting categories of drugs included in a formulary.

Upon successfully logging in, the clinician can be directed to a home page 56 where categories in which each of the drugs in the formulary 36 belong are displayed by the display 14 as shown in FIG. 9. Each category can be color coded in accordance with a drug labeling standard enacted by a governing body or trade organization or hospital policy, for example. For example, the "Induction Agent" category 58 is colored yellow. Touching the category in which the drug to be labeled is categorized causes the processing unit 22 of the label recognition terminal 10 to exclude from further consideration as potential matches to the drug all drugs in the formulary 36 not falling within the selected category. The filtered results, and optionally the categories appearing in the home page 56 can optionally be filtered, and limited to those potentially associated with any of the distinctive features utilized as Tier II, or even Tier III identifiers. Further, the results and optionally the categories can also be filtered based on the clinician logged into the label recognition terminal 10. For instance, a clinician whose practice involves the use of only induction agents and muscle relaxants may be presented with only those two categories on the home page 56. However, for the sake of discussion, such distinctive features are excluded from consideration in the present discussion.

Figure 10:
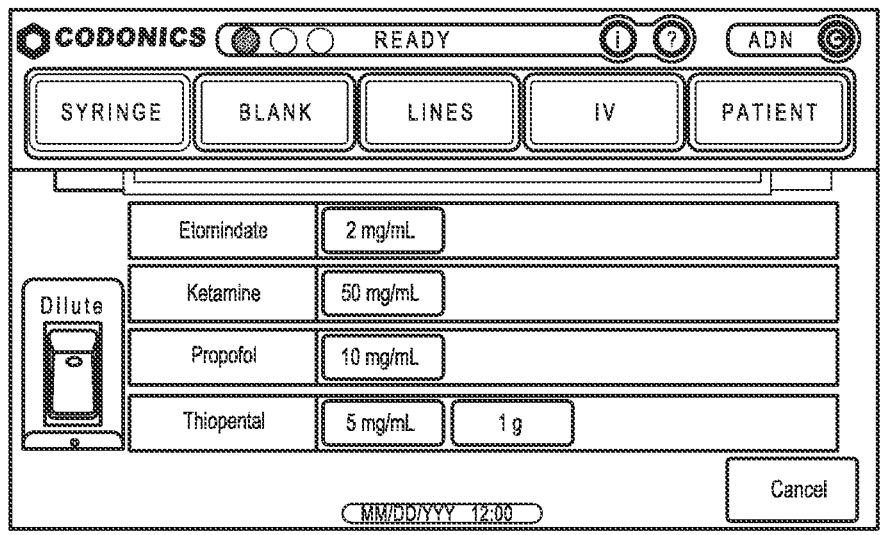
FIG. 10 shows an illustrative embodiment of a plurality of drugs included in the formulary categorized in a common class selected by a user.

FIG. 10 shows a plurality of induction agents displayed in response to selection of the Induction Agent category 58. Each of the plurality of induction agents displayed in FIG. 10 is presented along with at least one, and optionally a plurality of available concentrations. Selection (e.g., by touching) of just the appropriate concentration for one of the displayed induction agents amounts to a selection of both that drug and the selected concentration as the drug selected from the formulary 36.

In response to the identification of the drug selected from the formulary 36, a virtual label 16 is displayed by the display 14 along with an image 60 of the actual vial 21 selected, if included in the formulary 36 for the selected drug. An arrow 62 or other highlight can optionally be displayed to emphasize to the clinician a notable quality/quantity relating to the selected drug. For instance, if the formulary contains several different concentrations of the same drug, the arrow 62 can point to the concentration of the specific drug selected for confirmation that the appropriate concentration was selected by the clinician.

Figure 12:
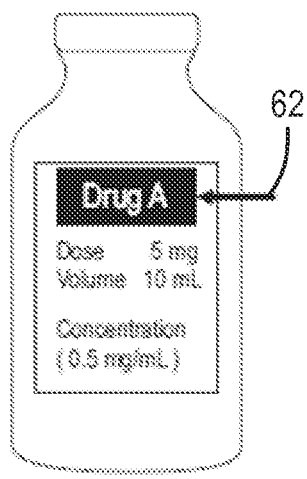
FIG. 12 shows an administrative tool for specifying the characteristics to be displayed as a generic image of a container instead of an image of the actual container.

The formulary 36 may lack a digital image 60 of the actual vial or other container for the drug selected, or the formulary may include a plurality of entries for the same drug obtained from different suppliers, where each such entry has a different appearance. Under such circumstances, each of the different vials and/or containers can be displayed, or the label recognition terminal 10 can display a generic representation of the vial or other appropriate container. For instance, a manager of the formulary 36 can utilize an administrative tool, a selection screen 70 of which is shown in FIG. 12, to specify the actual form of the container and the information to be highlighted. With this tool, the manager can specify for each entry in the formulary 36 the container type (e.g., vial, ampoule, IV bag, other) and the information included in the generic image to be highlighted by the arrow 62 or other marker. A message field 72 can also optionally be available to enable the manager to insert a custom message to be displayed along with the generic image in response to selection of the corresponding drug. In FIG. 12, the container for this particular formulary entry is identified as a vial, and the drug name is to be highlighted by the arrow 62. According to such embodiments, rather than the image of the actual vial, the generic image of the vial appearing in FIG. 12 can be displayed.

Figure 11:
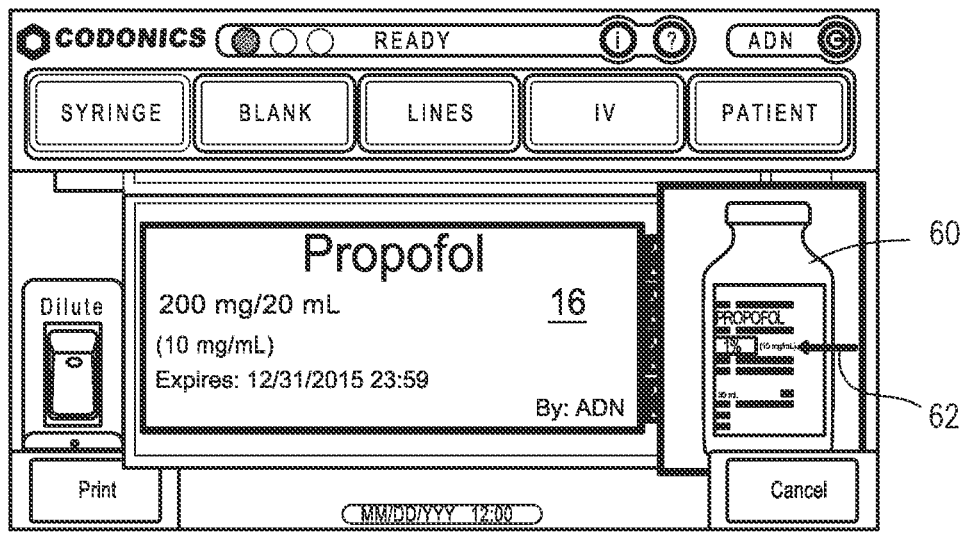
FIG. 11 shows an illustrative embodiment of a virtual label and an image of an actual vial captured by a camera displayed in response to a clinician's selection of the corresponding drug.
Figure 13:
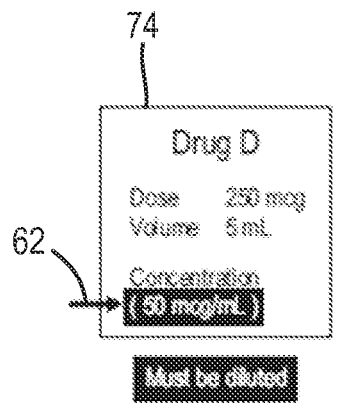
FIG. 13 shows another illustrative embodiment of an administrative tool for specifying the characteristics to be displayed as a generic image of a container instead of an image of the actual container, with a custom message included.
Figure 14:
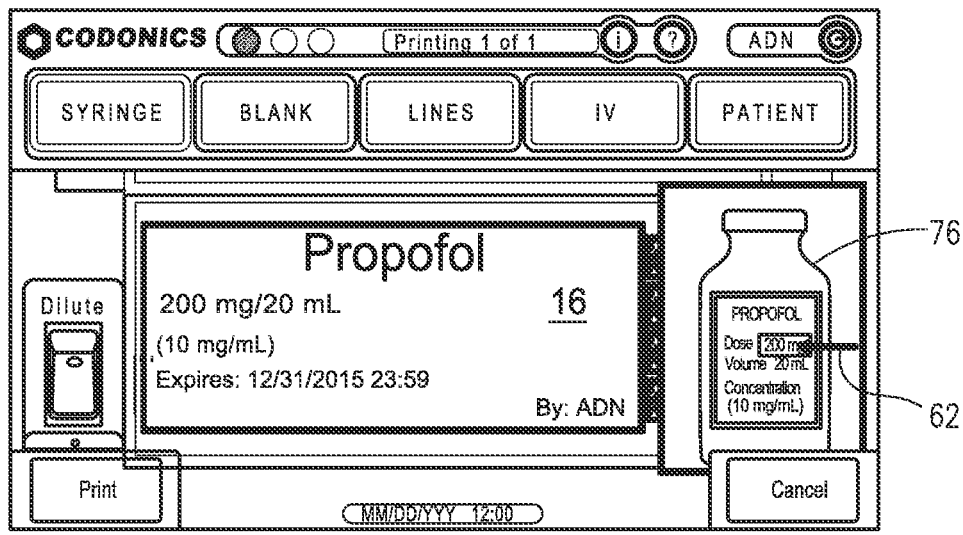
FIG. 14 shows an illustrative embodiment of a virtual label and a generic image representing a vial in response to a clinician's selection of the corresponding drug.

Similarly, in FIG. 13, the container is selected as "other", meaning that the container is not one of the specific containers listed, and the concentration is selected as being the information to be highlighted. Additionally, the custom message "Must be diluted" has been added to the message field 72. When the drug corresponding to this entry is selected, a generic label 74 is displayed instead of the shape representative of a specific container in the generic image displayed in the place of the image 60 of the actual container. Also, when the generic label 74 is displayed, concentration is highlighted by the arrow 62 and the custom message "Must be diluted" entered into the message field 70 is also automatically presented adjacent to the image. The virtual label 16 displayed adjacent to the generic image 76 of a vial is shown in FIG. 14, as compared with the image 60 of the actual vial as shown in FIG. 11.

Figure 15:
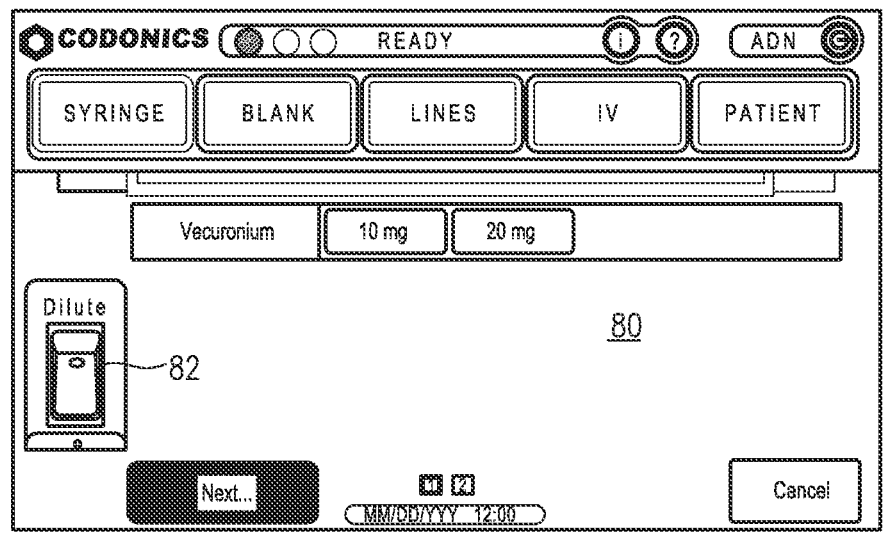
FIG. 15 shows an illustrative embodiment of a solid drug including a plurality of different weights available in the formulary to be reconstituted.
Figure 16:
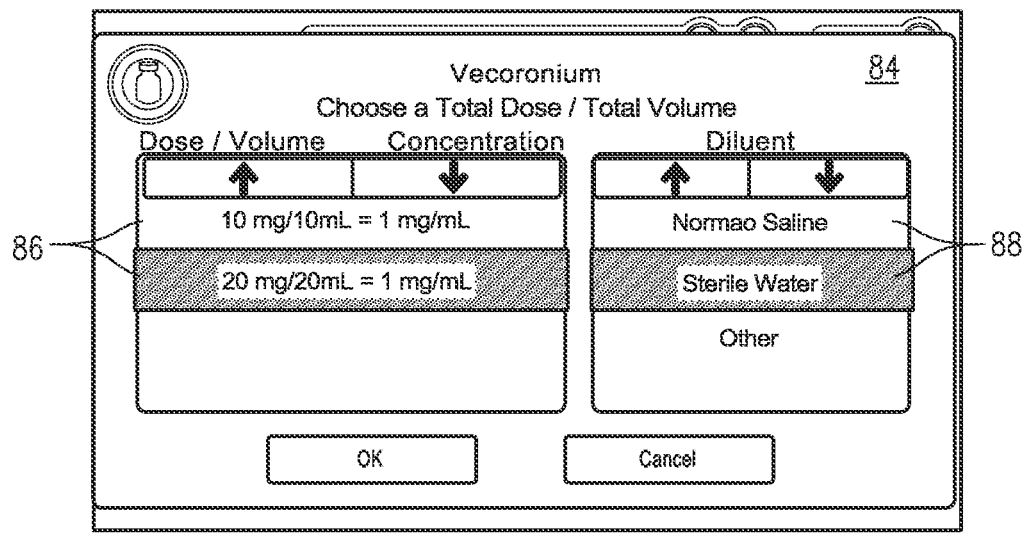
FIG. 16 shows an illustrative embodiment of a reconstitution screen from which a desired total dose/total volume can be selected along with a desired diluent.
Figure 17:
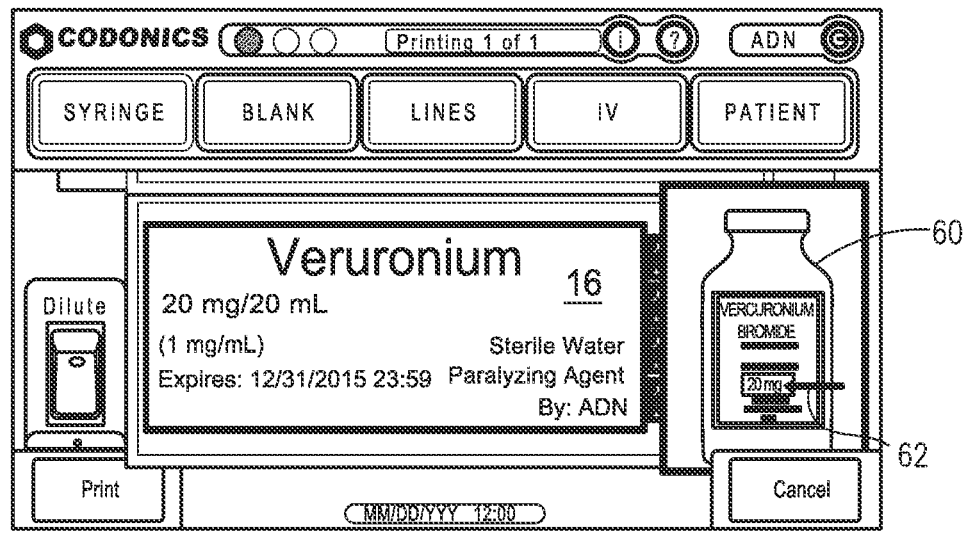
FIG. 17 shows an illustrative embodiment of a virtual label and an image of an actual vial storing the solid drug captured by a camera displayed in response to a clinician's selection of the corresponding drug.

The description to this point has focused primarily on identifying and selecting a vial of a liquid. However, drugs in solid form will often be reconstituted with a liquid diluent to be injected into the patient. Selecting the dosage of the drug as represented by the weight of the container in the clinician's possession from the display 80 shown in FIG. 15 selects not only the container with that quantity of the drug, but also the identity of the drug. The "Dilute" soft switch 82 has also been activated by the clinician in FIG. 15 to begin the process of selecting the total dose/total volume and diluent to be used for the reconstitution. From the dilution window 84 of FIG. 16, the clinician selects the total dose/total volume 86 to be prepared from among the options for the acceptable concentrations, and the diluent 88 to be used. Once the total dose/total volume 86 and the diluent 88 have been selected and confirmed, the virtual label 16 is displayed along with the image 60 of the actual container or the generic image described above and the arrow 62 highlighting the value in the selected field for that drug entry.

Figure 18:
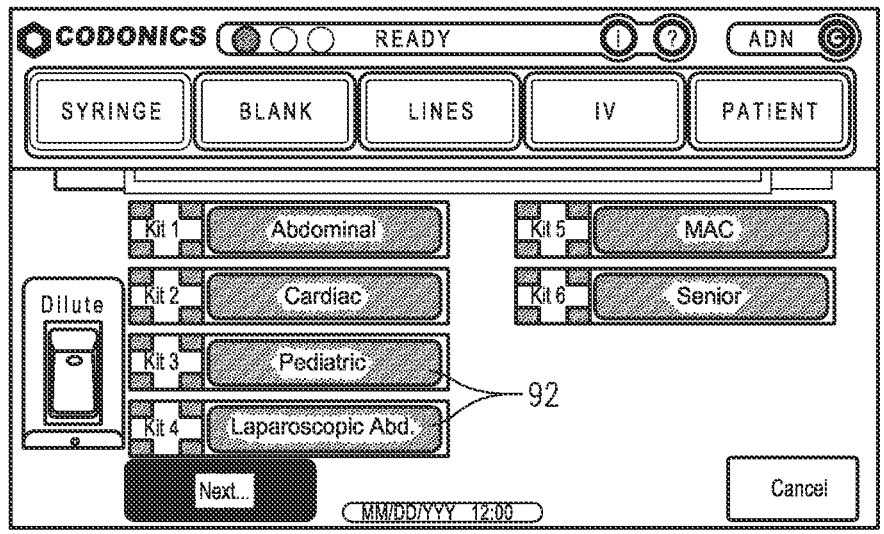
FIG. 18 shows an illustrative embodiment of a procedure screen including a plurality of different surgical procedures for which a kit of predefined drugs is available.
Figure 19:
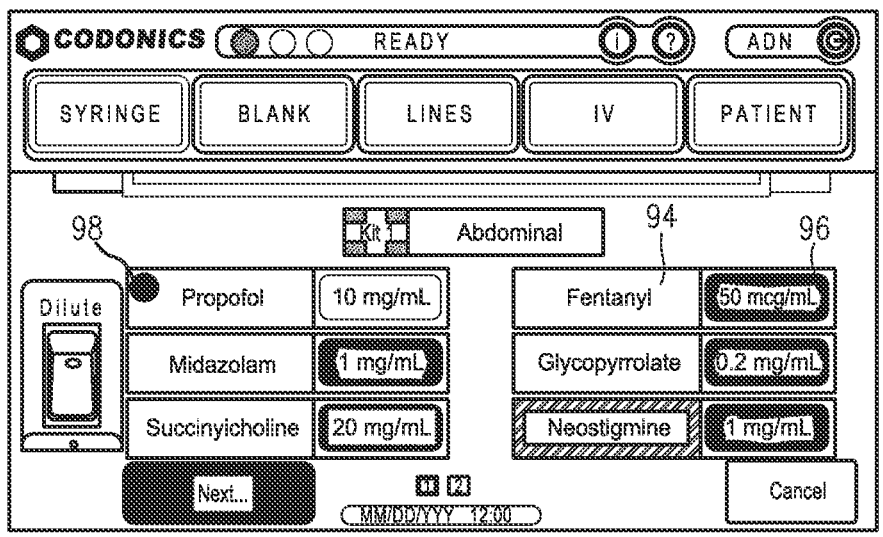
FIG. 19 shows an illustrative embodiment of the plurality of drugs for an abdominal surgical procedure, wherein the drug "Propofol" is identified as having already had a label printing.

Referring once again to FIG. 9, in addition to the categories of drugs presented to the clinician on the home page, the clinician can optionally be presented with a "Kits" category 90. Surgical centers that specialize in a particular type of surgical procedure may repeatedly administer the same combination of drugs to different patients, but at different quantities depending on the weight of each patient and possibly other factors. For example, the clinician can select the Kits category 90 to be presented with one or more types of surgical procedures 92 as shown in FIG. 18. Each surgical procedure can be selected to present the clinician with all of the drugs, in the desired concentrations for that selected procedure rather than require the clinician to manually select each drug. For example, selection of the "Laparoscopic Abdominal" procedure 92 in FIG. 18 presents the clinician with each of the drugs 94, in the appropriate concentrations 96, for that abdominal procedure as shown in FIG. 19. Once each drug is selected and the corresponding label 12 printed, that drug can be grayed out, an indicator 98 such as a check mark can be displayed adjacent to that drug, or the drug can otherwise be identified as having already had a label printed. Once a drug is selected from among those in the kit, however, the corresponding virtual label 16, optionally along with the image 60 of the actual vial or the generic image, can be displayed for confirmation purposes prior to printing as shown in FIGS. 11 and 14.

Regardless of how the specific drug and concentration is identified using the label recognition terminal 10, the label 12 (FIG. 1) bearing the label content illustrated with the virtual label 16 can be printed via the printer 26 to be applied to a syringe or other delivery container storing the drug removed from the vial or other container to be administered to the patient.

In another embodiment of the invention, a site-specific identifier such as a hospital billing code or unique drug identifier that is used for internal tracking and record keeping by the institution using the drug can be assigned to each drug vial or container via the administrative tool. This identifier, shown as the Container ID in FIG. 12, can be entered into the formulary for the respective drug entry by a party with the appropriate privileges into the appropriate field in the selection screen 70, to be stored in the computer-readable memory 24 of the label recognition terminal 10 or transferred to a other systems on the institution network using network adaptor 38 of the label recognition terminal 10 or encoded in an electronically readable format such as a barcode on a label 12. Thus, when the label 12 is printed, this container ID can be printed in human-readable characters, in a machine-readable format such as a barcode, or a combination thereof.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system for suggesting an identity of a drug within a drug container, the system comprising:
    an image capture circuit that captures an image of a portion of a label provided to the drug container;
    a non-transitory computer storage medium that stores a database comprising a plurality of drug entries and a plurality of features associated with each of the drug entries, wherein
        each of the plurality of features associated with each drug entry is suggestive of a drug identity corresponding to the drug entry but does not, alone, uniquely identify the drug identity; and
    a processor that evaluates content included in the image and identifies a candidate for the identity of the drug by evaluating each of the plurality of features included in the image and referencing the drug database, wherein
        the processor determines that an objective feature which, alone, is uniquely determinative of the identity of the drug is not present within the image by detecting an absence of a computer-readable barcode from the label provided to the drug container, and identifies the candidate in response to determining that the objective feature is not identifiable from the image.

2. The system of claim 1 further comprising:
    an output device that presents a user with the candidate; and
    an input device that is operable to receive confirmation entered by the user confirming that the candidate presented by the output device matches the identity of the drug.

3. The system of claim 2, wherein the processor generates a label comprising label content that comprises the identity of the dug in response to receiving said confirmation.

4. The system of claim 1, wherein the plurality of features comprise an optically-detectable characteristic appearing on the drug container, said optically-detectable characteristic comprising at least one of: a concentration, a weight, dilution information, manufacturer identity, label size, label shape, code, drug container size, and drug container shape.

5. The system of claim 1, wherein the processor performs an optical character recognition operation on the image to convert a portion of the image into text, and evaluates the text as one of the plurality of features for identifying the candidate.

6. The system of claim 1 further comprising an input device that receives a user-specified identity of the drug, wherein the processor determines a degree of certainty to which the candidate matches the identity of the drug, and requests entry of the user-specified identity when the degree of certainty does not exceed a threshold minimum certainty.

7. A method of suggesting an identity of a drug within a drug container based on an image of at least a portion of the drug container captured by an image capture device, the method comprising:
   evaluating the image and determining that an objective feature which, alone, is uniquely determinative of the identity of the drug is absent from the image;
   identifying, in the image, a plurality of features that each, individually, do not uniquely identify the drug, but are collectively suggestive of the identity of the drug;
   retrieving, from a database storing a plurality of drug entries and a plurality of distinctive features related to the drug container associated with each of the drug entries, a candidate for the identity of the drug based on a combination of the plurality of features included in the image;
   determining a probability that the candidate matches the identity of the drug within the drug container;
   comparing the probability to a threshold minimum probability; and
   requesting manual entry of a user-specified identity of the drug via an input device in response to determining that the probability is not greater than the threshold minimum probability.

8. The method of claim 7 further comprising:
   presenting the candidate to a user; and
   requesting manual entry of confirmation that the candidate matches the identity of the drug appearing on a label provided to the drug container.

9. The method of claim 8 further comprising:
   initiating printing of a label comprising label content comprising the identity of the dug in response to receiving said confirmation to be applied to another container that is to store the drug.

10. The method of claim 7, wherein said identifying the plurality of features comprises initiating an optical character recognition operation on the image to convert a portion of the image into text, and evaluating the text as one of the plurality of features for identifying the candidate.

11. The method of claim 7, wherein said determining that the objective feature is absent from the image comprises detecting an absence of a computer-readable barcode from a portion of the label provided to the drug container appearing in the image.

12. A system for suggesting an identity of a drug within a drug container, the system comprising:
   an image capture circuit that captures an image of a portion of a label provided to the drug container;
   a non-transitory computer storage medium that stores a database comprising a plurality of drug entries and a plurality of features associated with each of the drug entries, wherein
      each of the plurality of features associated with each drug entry is suggestive of a drug identity corresponding to the drug entry but does not, alone, uniquely identify the drug identity;
   a processor that evaluates content included in the image and identifies a candidate for the identity of the drug by evaluating each of the plurality of features included in the image and referencing the drug database; and
   an input device that receives a user-specified identity of the drug, wherein
      the processor determines a degree of certainty to which the candidate matches the identity of the drug, and requests entry of the user-specified identity when the degree of certainty does not exceed a threshold minimum certainty.

13. The system of claim 12 further comprising:
   an output device that presents a user with the candidate; and
   an input device that is operable to receive confirmation entered by the user confirming that the candidate presented by the output device matches the identity of the drug.

14. The system of claim 12, wherein the plurality of features comprise an optically-detectable characteristic appearing on the drug container, said optically-detectable characteristic comprising at least one of: a concentration, a weight, dilution information, manufacturer identity, label size, label shape, code, drug container size, and drug container shape.

15. The system of claim 12, wherein the processor performs an optical character recognition operation on the image to convert a portion of the image into text, and evaluates the text as one of the plurality of features for identifying the candidate.

16. A method of suggesting an identity of a drug within a drug container based on an image of at least a portion of the drug container captured by an image capture device, the method comprising:
   evaluating the image and determining that an objective feature which, alone, is uniquely determinative of the identity of the drug is absent from the image;
   identifying, in the image, a plurality of features that each, individually, do not uniquely identify the drug, but are collectively suggestive of the identity of the drug;
   retrieving, from a database storing a plurality of drug entries and a plurality of distinctive features related to the drug container associated with each of the drug entries, a candidate for the identity of the drug based on a combination of the plurality of features included in the image;
   presenting the candidate to a user;
   requesting manual entry of confirmation that the candidate matches the identity of the drug appearing on a label provided to the drug container; and
   initiating printing of a label comprising label content comprising the identity of the dug in response to receiving said confirmation to be applied to another container that is to store the drug.

17. The method of claim 16, wherein said identifying the plurality of features comprises initiating an optical character recognition operation on the image to convert a portion of the image into text, and evaluating the text as one of the plurality of features for identifying the candidate.

18. The method of claim 16, wherein said determining that the objective feature is absent from the image comprises detecting an absence of a computer-readable barcode from a portion of the label provided to the drug container appearing in the image.

19. A method of suggesting an identity of a drug within a drug container based on an image of at least a portion of the drug container captured by an image capture device, the method comprising:
   evaluating the image and determining that an objective feature which, alone, is uniquely determinative of the identity of the drug is absent from the image;

identifying, in the image, a plurality of features that each, individually, do not uniquely identify the drug, but are collectively suggestive of the identity of the drug; and retrieving, from a database storing a plurality of drug entries and a plurality of distinctive features related to the drug container associated with each of the drug entries, a candidate for the identity of the drug based on a combination of the plurality of features included in the image, wherein said determining that the objective feature is absent from the image comprises detecting an absence of a computer-readable barcode from a portion of the label provided to the drug container appearing in the image.

20. The method of claim 19, wherein said identifying the plurality of features comprises initiating an optical character recognition operation on the image to convert a portion of the image into text, and evaluating the text as one of the plurality of features for identifying the candidate.

* * * * *